US00PP15745P2

(12) United States Plant Patent
Olesen et al.

(10) Patent No.: US PP15,745 P2
(45) Date of Patent: May 3, 2005

(54) ***CLEMATIS* PLANT NAMED 'EVIPO008'**

(50) Latin Name: *Clematis viticella*
Varietal Denomination: EVIpo008

(75) Inventors: Mogens N. Olesen, Fredensborg (DK); Raymond J. Evison, St. Sampsons (GB)

(73) Assignee: Poulsen Roser A/S, Fredensborg (DK)

( * ) Notice: Subject to any disclaimer, the term of this patent is extended or adjusted under 35 U.S.C. 154(b) by 12 days.

(21) Appl. No.: 10/877,732

(22) Filed: Jun. 25, 2004

(51) Int. Cl.[7] ..... A01H 5/00
(52) U.S. Cl. ..... Plt./228
(58) Field of Search ..... Plt./228

*Primary Examiner*—Kent Bell

(57) ABSTRACT

A new *Clematis* cultivar which is well suited to propagation in glasshouses. With a tall growth habit, profuse, lavender double flowers, and continuous summer flowering. The variety successfully propagates from softwood cuttings and is suitable for cultivation in commercial glasshouses. This new and distinct variety has shown to be uniform and stable in the resulting generations from propagation.

2 Drawing Sheets

Botanical classification: Genus—*Clematis*. Species—*viticella*.

Variety denomination: 'EVIpo008'.

COMMERCIAL CLASSIFICATION

Early flowering, large flowered cultivar.

SUMMARY OF THE INVENTION

The present invention constitutes a new and distinct variety of *Clematis* which originated from a chance pollination between the female plant 'EVItwo', described and illustrated in U.S. Plant Pat. No. 10,167 dated Dec. 30, 1997, and an unknown male pollen parent plant.

The new *clematis* may be distinguished from its female seed parent, 'EVItwo', by the following combination of characteristics:

1. Flowers of 'EVItwo' are white, while those of 'EVIpo008' are lavender purple.
2. Flowers of 'EVItwo' have 12 tepals on average, while flowers of 'EVIpo008' have 40 to 60 tepals.

The seed resulting from the chance pollination was planted in a controlled environment. The resulting seedlings were evaluated.

The objective of the selection of this *Clematis* variety for commercial glasshouse and nursery culture was to create a new and distinct variety with unique qualities that this variety has:

1. Exceptional violet colored flowers;
2. Flowers that have double tepalage;
3. Plants which re-flower readily;
4. Desirable glasshouse production characteristics such as ease of propagation and good flowering characteristics.

These qualities required improvement in *Clematis* varieties that were in commercial cultivation and the objectives have been substantially achieved in the new variety, as evidenced by the unique combination of characteristics that are present in 'EVIpo008' which distinguish it from all other varieties of which we are aware.

The seeds from the aforementioned chance pollination were germinated and evaluations of the resulting seedling plants were conducted in a controlled environment. As a result, 'EVIpo008' was selected by Raymond J. Evison and Mogens N. Olesen in their *Clematis* development program in Domarie Vineries Les Sauvagees, St. Sampsons, Guernsey, Channel Islands, United Kingdom in April 1993.

Asexual reproduction of 'EVIpo008' by cuttings was first done by Raymond J. Evison and Mogens N. Olesen in Domarie Vineries Les Sauvagees, St. Sampsons, Guernsey, Channel Islands, United Kingdom in April 1995. This initial and subsequent propagations have demonstrated that the characteristics of 'EVIpo008' are true to type and are transmitted from one generation to the next.

BRIEF DESCRIPTION OF THE DRAWING

The accompanying color illustrations show as true as is reasonably possible to obtain in color photographs of this type:

FIG. 1.2 Flowers, upon opening;

FIG. 1.3 Stem, leaves, bud at ¼ opening, bud closed;

FIG. 1.4 Single leaf;

FIG. 1.5 Stem and juvenile foliage.

DETAILED DESCRIPTION OF THE VARIETY

Figure 1:
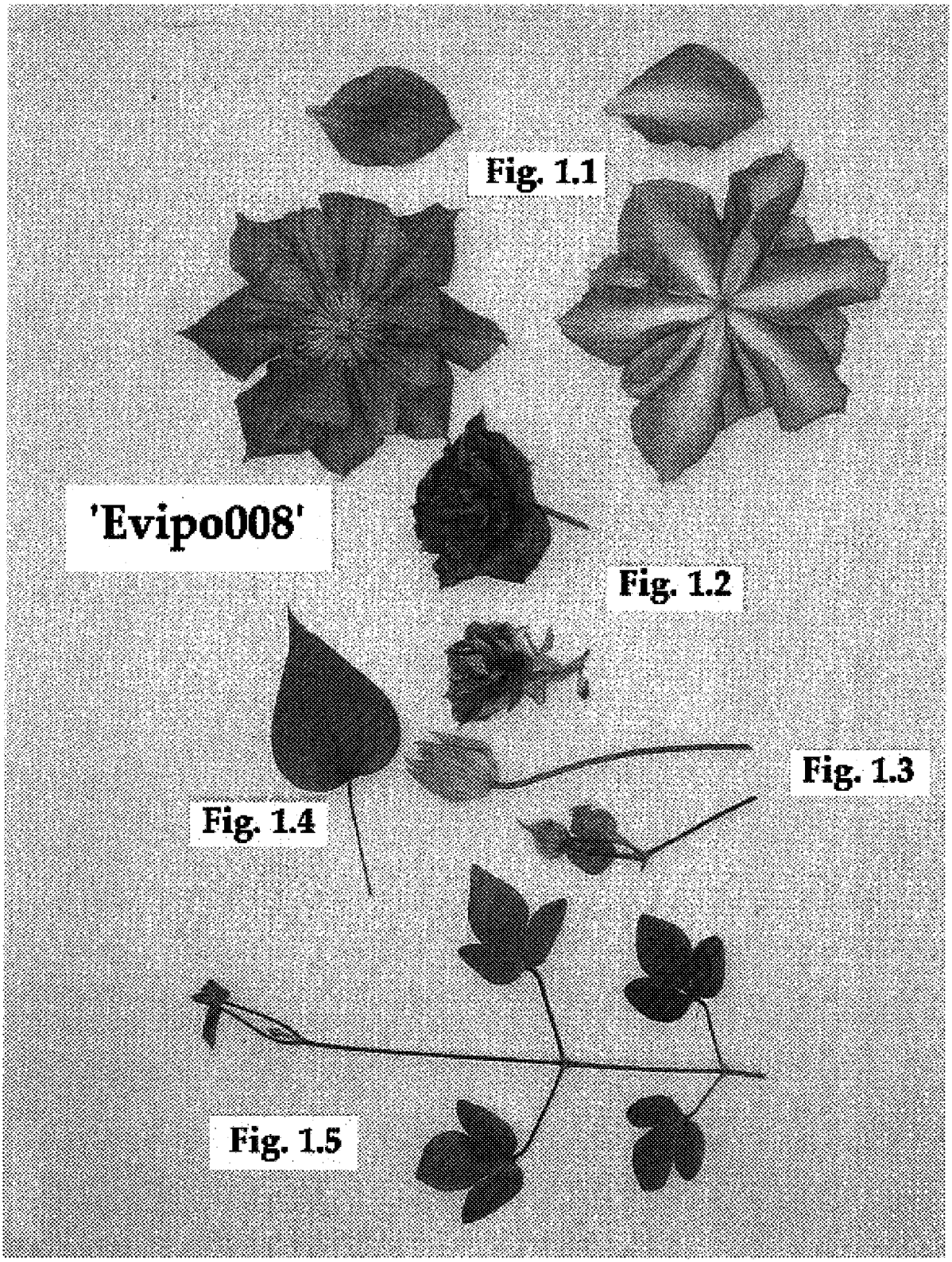
FIG. 1.1 Upper and lower surface of open flower, and tepals detached.
Figure 2:
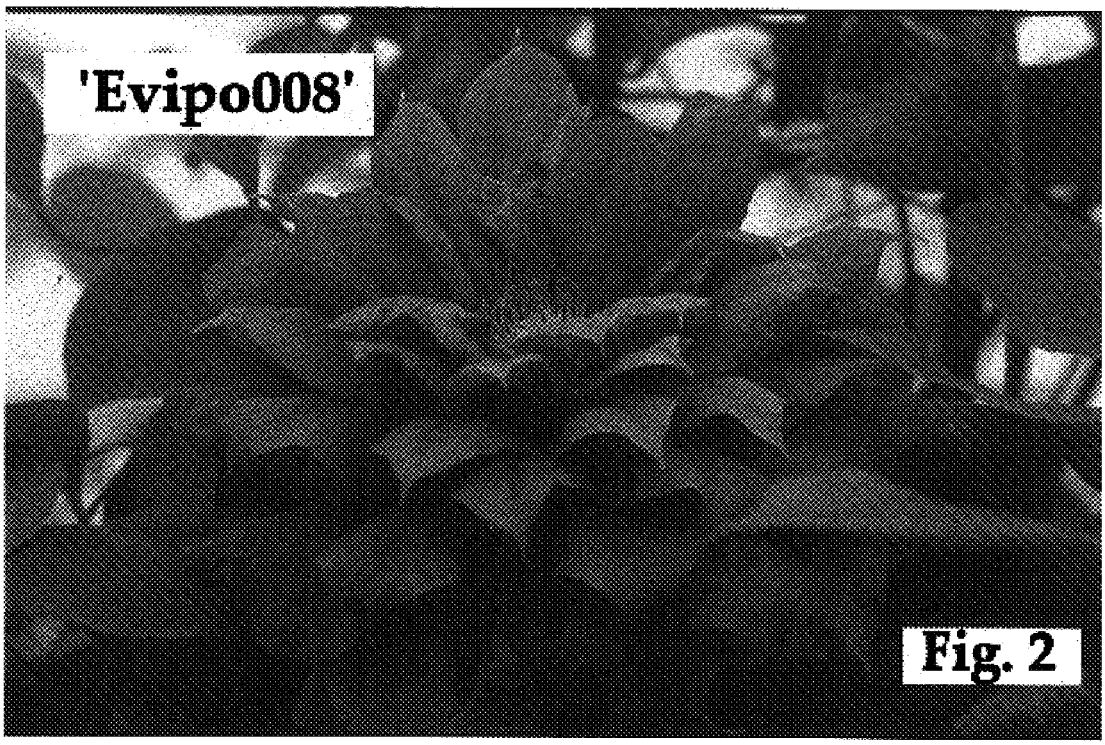
FIG. 2 Open flower, side view.

The following is a detailed description of 'EVIpo008', as observed in its growth throughout the flowering period in glasshouses at Domarie Vineries Les Sauvagees, St. Sampsons, Guernsey, Channel Islands, United Kingdom. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001.

For a comparison, the nearest existing *Clematis* variety is 'Belle of Woking' non-patented variety. Chart 1 details several physical characteristics of 'EVIpo008' and the comparison variety.

CHART 1

| | 'EVIpo008' | 'Belle of Woking' |
|---|---|---|
| Repeat flowering | good | poor |
| Tepal color | Violet Blue 91A | Purple 76A |

FLOWER AND FLOWER BUD

Blooming habit: Recurrent. The first flowering period is from April to May. Later flowering occurs in September and October. Flowering can be continuous if plants are pruned accordingly.

Flower bud:
- *Size.*—25 to 35 mm in length. Bud diameter is 20 to 25 mm.
- *Bud form.*—Short ovoid.
- *Bud color.*—Green Group 138B at ¼ opening.

Peduncle:
- *Surface.*—Smooth.
- *Length.*—150 to 200 mm.
- *Strength.*—Strong.

Receptacle: None to observe.

Flower arrangement:
- *Location on vine.*—Flowering occurs on previous season's as well as current season's growth.
- *Borne.*—In compound cymes consisting of 3 to 5 flowers.

Flower bloom:
- *Size.*—90 to 120 mm in diameter. 60 mm in depth.
- *Profile.*—Upon opening, flowers are globular. After opening flowers are globular.
- *Color.*—Upon opening: Upper and lower surfaces of tepals are Violet Group 90A. After opening: Upper surface is Violet Group 91A. Lower surface is Violet Group 91A with a central bar extending the length of the tepal, White Group 155A in color.
- *Fragrance.*—None.
- *Lasting quality on plant.*—15 to 20 days.
- *Lasting quality as a cut flower.*—5 to 8 days.

Tepals:
- *Quantity.*—Average range is 40 to 60 tepals.
- *Size.*—40 to 60 mm in length by 25 to 35 mm wide.
- *Shape.*—Individual tepal shape is ovate.
- *Cross section.*—Reflexed.
- *Margins.*—Entire.
- *Undulation of margin.*—Slight undulations 2 to 3 times along the length of tepals.
- *Tepal apex.*—Acute.
- *Recurvature of tip.*—Recurved.
- *Persistence.*—Tepals drop off cleanly.
- *Arrangement.*—Tepals are arranged regularly.

Reproductive organs:
- *Arrangement.*—Open.
- *Pollen.*—Quantity: Average. Color: Creamy white, nearest color is White Group 155A.
- *Anthers.*—Size: 10 mm in length. Color: Yellow Group 8D. Quantity: 90 to 100.
- *Filaments.*—Color: White Group 155A. Length: 5 to 10 mm.
- *Pistils.*—Quantity: 40 to 50.
- *Stigmas.*—Same position relative to the length of the filaments and the height of the anthers.
- *Styles.*—Color: White Group N157A. Length: 15 mm.

Seed head characteristics:
- *Size.*—Collectively, seeds form a globular cluster 35 to 40 mm wide.
- *Shape.*—Individual seeds are 5 to 6 mm in diameter, and are circular to tear shaped, with an elongate plumule of 30 to 40 mm in length.

PLANT

Plant form: Climbing.

Plant growth: Moderate vigor.

Size: Seasons growth attains 2.0 meters in height. Average spread is 1 meter.

Hardiness: Trials to date show the variety hardy in USDA Zones 4–9.

Stems:
- *Color.*—Young wood: Greyed Red Group 178B. Older wood: Greyed Orange Group 165C.
- *Internodes.*—Shape: Cylindrical. Length: 100 to 150 mm.
- *Surface.*—Young wood: Smooth. Older wood: Smooth.

Plant foliage:
- *Leaf characteristics.*—Deciduous.
- *Mature leaf form.*—Normally compound trifoliate leaves. Occasionally, leaves appear in single, simple form.
- *Compound leaf size.*—200 mm (l)×150 mm (w).
- *Abundance.*—Generally, there are 8 leaves per 10 cm of stem.
- *Color.*—Upper surfaces of mature foliage are Green Group 137A. Lower surfaces are Green Group 137C. Upper surfaces of new foliage are Green Group 143A. Lower surfaces are Green Group 143C.

Plants leaves and leaflets:
- *Stipules.*—Absent.
- *Petioles.*—Size: 60 to 80 mm in length. Color: Red-Purple Group 60A. Clasping: By leaf petiole.
- *Petioloule.*—Length: 25 to 35 mm. Color: Green Group 137B turning to Red-Purple Group 60A.
- *Leaf edge.*—Terminal leaflet margin is entire.
- *Leaflet shape.*—General shape: Ovate. Base: Rounded. Apex: Acute.
- *Leaflet size.*—70 mm in length by 50 mm wide.
- *Surface.*—Upper side: Smooth. Lower side: Smooth with protruding venation.
- *Thickness.*—Moderate.
- *Glossiness.*—Upper and lower side usually matte in appearance.

Disease resistance: Subject to any disease that normally attacks the species, however the variety is more tolerant to *Botrytis* than some *Clematis* with the double flower form.

It is claimed:

1. A new and distinct variety of *Clematis* plant named 'EVIpo008', described and illustrated herein as a distinct and novel *clematis* variety due to its abundant lavender flowers with good keepability, attractive long lasting foliage and compact growth, year round flowering under glasshouse conditions, suitability for production from softwood cutting in pots, durable flowers and foliage which make the variety suitable for distribution in the floral industry.

* * * * *

Fig. 1.1
'Evipo008'
Fig. 1.2
Fig. 1.3
Fig. 1.4
Fig. 1.5